United States Patent
Raghunath et al.

(10) Patent No.: US 10,189,014 B2
(45) Date of Patent: Jan. 29, 2019

(54) SOLID PHOSPHORIC ACID CATALYSTS

(71) Applicant: CLARIANT CORPORATION, Louisville, KY (US)

(72) Inventors: Malati Raghunath, Palo Alto, CA (US); Aaron Miller, San Ramon, CA (US); Claus G Lugmair, Santa Cruz, CA (US); Anthony Volpe, Santa Clara, CA (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 15/661,088

(22) Filed: Jul. 27, 2017

(65) Prior Publication Data

US 2018/0036720 A1 Feb. 8, 2018

Related U.S. Application Data

(60) Provisional application No. 62/370,819, filed on Aug. 4, 2016.

(51) Int. Cl.
| | |
|---|---|
| *B01J 37/08* | (2006.01) |
| *B01J 27/182* | (2006.01) |
| *B01J 35/02* | (2006.01) |
| *C07C 2/18* | (2006.01) |
| *C07C 2/70* | (2006.01) |

(Continued)

(52) U.S. Cl.
CPC ............ *B01J 27/182* (2013.01); *B01J 27/14* (2013.01); *B01J 27/16* (2013.01); *B01J 35/02* (2013.01); *B01J 37/0009* (2013.01); *C07C 2/00* (2013.01); *C07C 2/18* (2013.01); *C07C 2/70* (2013.01); *C07C 2527/173* (2013.01)

(58) Field of Classification Search
CPC ...... B01J 27/182; B01J 27/186; B01J 27/188; B01J 35/02; B01J 37/08; C07C 2/18; C07C 2/70; C07C 2527/173
USPC ........................................................ 502/214
See application file for complete search history.

(56) References Cited

U.S. PATENT DOCUMENTS

| | | | |
|---|---|---|---|
| 1,993,513 A | 3/1935 | Ipatieff | |
| 2,569,092 A * | 9/1951 | Deering | B01J 21/16 |
| | | | 502/209 |

(Continued)

FOREIGN PATENT DOCUMENTS

| | | |
|---|---|---|
| CN | 1506158 | 6/2004 |
| EP | 0447705 | 3/1990 |

(Continued)

*Primary Examiner* — Patricia L. Hailey

(57) ABSTRACT

The present disclosure relates to solid phosphoric acid (SPA) catalysts useful in the conversion of hydrocarbons, such as the oligomerization of olefins, to methods for making such SPA catalysts, and to methods for converting hydrocarbons by contacting hydrocarbons with such catalyst. For example, in certain embodiments, the disclosure provides a calcined solid phosphoric acid catalyst composition that includes phosphoric acid and silicon phosphates, and in which (i) one or more promoters each selected from the group consisting of boron, bismuth, tungsten, silver and lanthanum is present; (ii) the composition is a calcined product of a formable mixture including silica-alumina clay, silica fiber and/or silica alumina fiber; or (iii) the composition is a calcined product of a formable mixture including fumed silica.

22 Claims, 5 Drawing Sheets

(51) Int. Cl.
  *B01J 27/14* (2006.01)
  *B01J 27/16* (2006.01)
  *B01J 37/00* (2006.01)
  *C07C 2/00* (2006.01)

(56) References Cited

U.S. PATENT DOCUMENTS

| | | | |
|---|---|---|---|
| 2,824,149 A * | 2/1958 | Corner | C07C 2/18 |
| | | | 502/214 |
| 3,044,964 A | 7/1962 | Morrell | |
| 3,112,350 A | 9/1963 | Bielawski | |
| 3,661,801 A | 5/1972 | Gutmann | |
| 3,758,627 A | 9/1973 | Juguin | |
| 4,334,118 A * | 6/1982 | Manning | C07C 2/18 |
| | | | 502/214 |
| 4,619,908 A | 10/1986 | Cheng | |
| 4,912,279 A | 3/1990 | Wilcher | |
| 4,946,815 A | 8/1990 | Chao | |
| 5,043,509 A | 8/1991 | Imai | |
| 5,059,737 A | 10/1991 | Chao | |
| 5,081,086 A | 1/1992 | Wilcher | |
| 5,177,283 A | 1/1993 | Ward | |
| 6,040,262 A | 3/2000 | Fougret | |
| 6,313,323 B1 * | 11/2001 | Werner | B01J 27/16 |
| | | | 549/368 |
| 7,557,060 B2 | 7/2009 | Xu | |
| 9,205,412 B2 | 12/2015 | Miller | |
| 9,206,357 B2 | 12/2015 | Hamilon | |
| 9,403,149 B2 | 8/2016 | Turbeville | |
| 2009/0005623 A1 * | 1/2009 | Xu | B01J 27/182 |
| | | | 585/470 |
| 2013/0053599 A1 * | 2/2013 | Weiner | B01J 37/03 |
| | | | 560/211 |

FOREIGN PATENT DOCUMENTS

| | | |
|---|---|---|
| EP | 0371938 | 6/1990 |
| EP | 0570070 | 5/1993 |

* cited by examiner

SOLID PHOSPHORIC ACID CATALYSTS

BACKGROUND OF THE DISCLOSURE

Field of the Disclosure

This disclosure relates generally to solid catalyst materials. More particularly, the present disclosure relates to solid phosphoric acid (SPA) catalysts useful in the conversion of hydrocarbons, such as the oligomerization of olefins, to methods for making such SPA catalysts, and to methods for converting hydrocarbons comprising contacting hydrocarbons with such catalysts.

Technical Background

Solid phosphoric acid (SPA) catalysts are known for their usefulness in various hydrocarbon conversion processes, such as the alkylation of benzene and other aromatic hydrocarbons with olefins to produce alkyl aromatic products such as cumene and ethylbenzene, and the oligomerization or polymerization of olefins, for example, the oligomerization of light olefins to heavier olefins and paraffins ("polymer gasoline" or "polygas"). Conventional SPA catalysts are made by calcining mixtures of one or more phosphoric acids with one or more siliceous support material sources. This typically results in a complex mixture of phosphoric acids (e.g., orthophosphoric acid, pyrophosphoric acid, triphosphoric acid), silicon phosphates formed by reaction of phosphoric acids with the siliceous support material source, and, in some cases, siliceous support material. The operative catalyst is typically a layer of liquid phosphoric acids on solid silicon phosphates; silicon orthophosphate may act as a reservoir of orthophosphoric acid, which is a desirable catalytic material.

However, conventional SPA catalysts are not particularly robust, and can degrade over time (e.g., via deactivation, disintegration, etc.). Accordingly, over time a process using a conventional SPA catalyst can require increased operational temperatures, lower reactor space velocities to maintain acceptable conversion levels. In turn, higher temperatures result in undesirable by-products and increased rates of coking of the catalyst, and slower flow rates result in lower overall rates of production. Accordingly, the use of conventional SPA catalysts requires relatively frequent reactor shut-downs in order to replace the SPA catalyst, all resulting in a decrease in overall process efficiency.

Accordingly, there remains a need for a more robust SPA catalyst with improvements in one or more areas of activity, crush strength, crystallinity, acidity (surface and/or total), and porosity.

SUMMARY OF THE DISCLOSURE

One aspect of the disclosure relates to a calcined solid phosphoric acid catalyst composition comprising:
  one or more phosphoric acids
  one or more silicon phosphates;
  optionally, one or more additional inorganic phosphates; and
  optionally, a siliceous support material,
  wherein the amount of phosphate in the calcined solid phosphoric acid catalyst composition is within the range of about 30 wt. % to about 85 wt. %, calculated as $P_2O_5$ on a calcined basis; and
  the amount of silicon in the calcined solid phosphoric acid catalyst composition is within the range of about 15 wt. % to about 70 wt. % calculated as $SiO_2$ on a calcined basis; and
  wherein
    (i) the calcined solid phosphoric acid catalyst composition includes one or more promoters each selected from the group consisting of boron, bismuth, tungsten, silver and lanthanum, present in an amount within the range of about 0.015 wt. % to about 5 wt. %, calculated as oxide on a calcined basis;
    (ii) the calcined solid phosphoric acid catalyst composition is the calcined product of a formable mixture comprising one or more of a silica-alumina clay, a silica fiber material and a silica-alumina fiber material, present in the formable mixture in an amount within the range of about 0.1 wt. % to about 15 wt. % on a calcined basis; or
    (iii) the calcined solid phosphoric acid catalyst composition is the calcined product of a formable mixture comprising fumed silica, present in the formable mixture in an amount within the range of about 0.1 wt. % to about 15 wt. % on a calcined basis.

Another aspect of the disclosure relates to a method for preparing a solid phosphoric acid catalyst composition, the method comprising
  providing a formable mixture comprising
    a phosphate source present in an amount within the range of about 50 wt. % to about 85 wt. % on a calcined weight basis;
    a siliceous support material source present in an amount within the range of about 15 wt. % to about 50 wt. % on a calcined weight basis; and
    at least one of
      (i) one or more promoters each selected from the group consisting of boron, bismuth, tungsten, silver and lanthanum, present in an amount within the range of about 0.015 wt. % to about 5 wt. % on a calcined weight basis;
      (ii) a silica-alumina clay and/or an alumina-silica fiber, present in an amount within the range of about 0.1 wt. % to about 15 wt. % on a calcined weight basis; and
      (iii) fumed silica present in an amount within the range of about 0.1 wt. % to about 15 wt. % on a calcined weight basis;
  forming (e.g., by extruding, tableting or pelletizing) the mixture; and
  calcining the formed (e.g., extruded, tableted or pelletized) mixture.

Another aspect of the disclosure is a catalyst composition made by a method as described herein.

Another aspect of the disclosure is a method for converting hydrocarbons (e.g., olefin oligomerization or aromatic hydrocarbon alkylation), comprising contacting a hydrocarbon feed with a catalyst composition as described herein.

DETAILED DESCRIPTION

Figure 1:
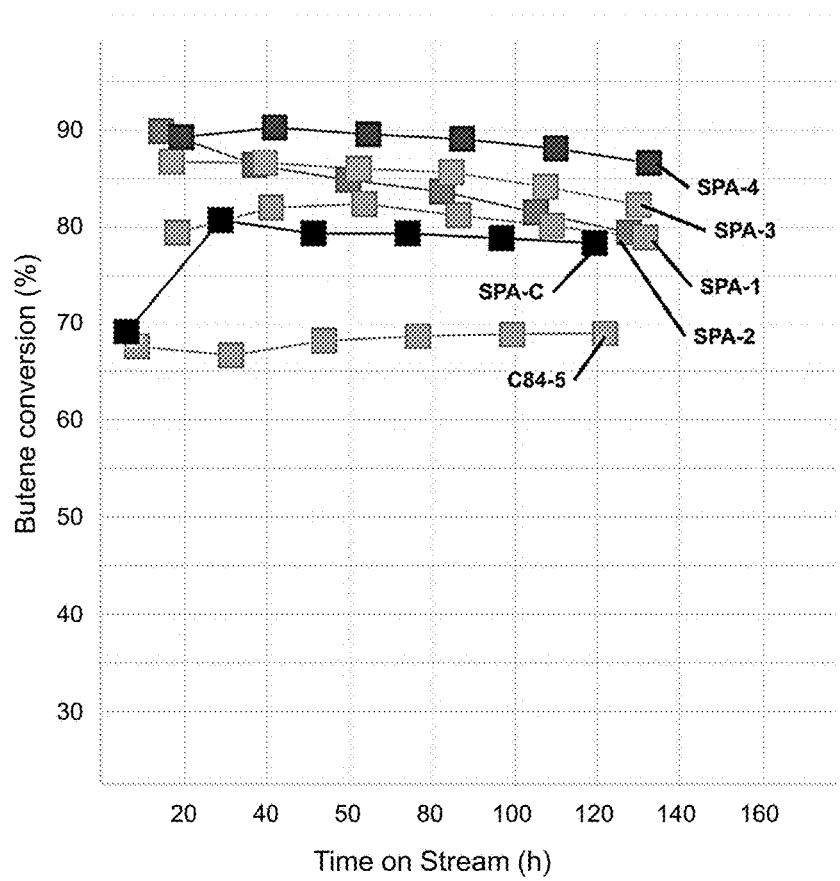
FIG. 1 is a graph of the 1-butene oligomerization performance of particular example promoter-modified SPA catalysts (SPA-1, SPA-2, SPA-3, and SPA-4) compared with particular comparative unmodified SPA catalysts (SPA-C and C84-5), as described in Example 4.
Figure 2:
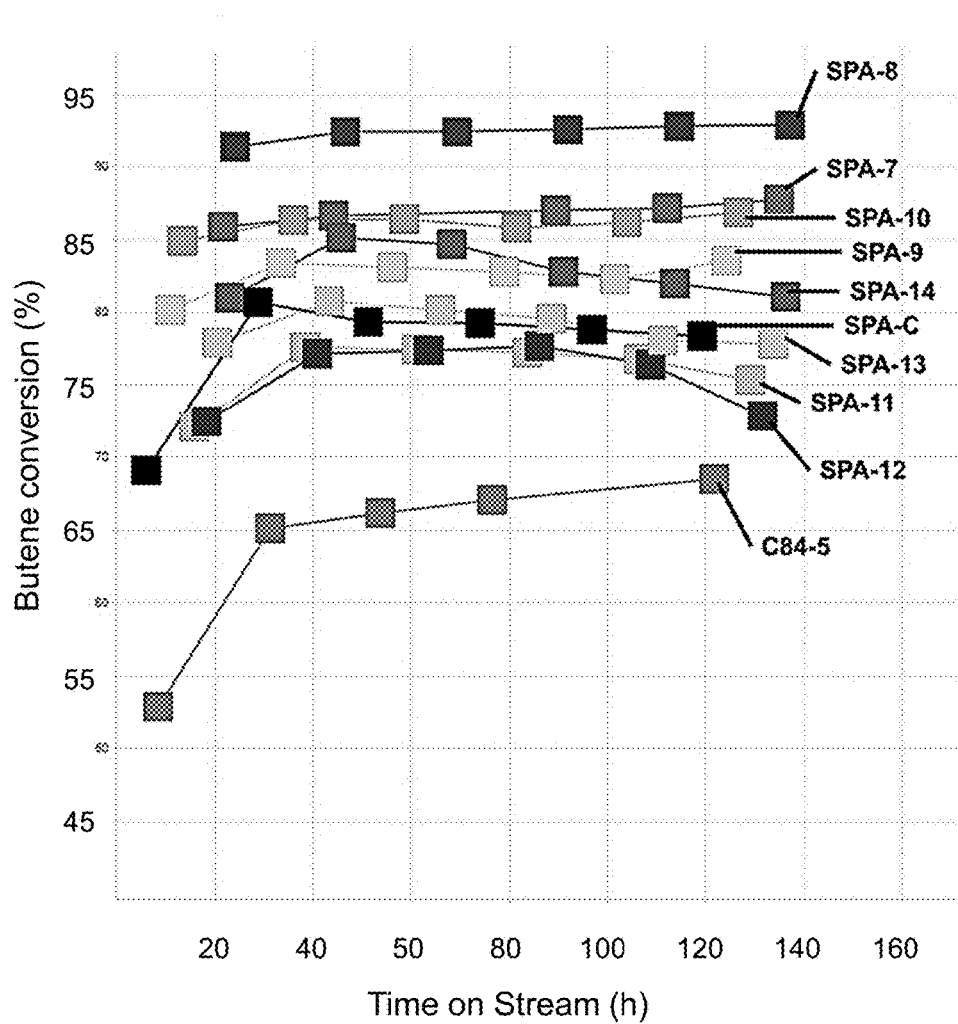
FIG. 2 is a graph of the 1-butene oligomerization performance of particular example support-modified SPA catalysts (SPA-7, SPA-8, SPA-9, SPA-10, SPA-11, SPA-12, SPA-13, and SPA-14) compared with particular comparative unmodified SPA catalysts (SPA-C and C84-5), as described in Example 4.
Figure 3:
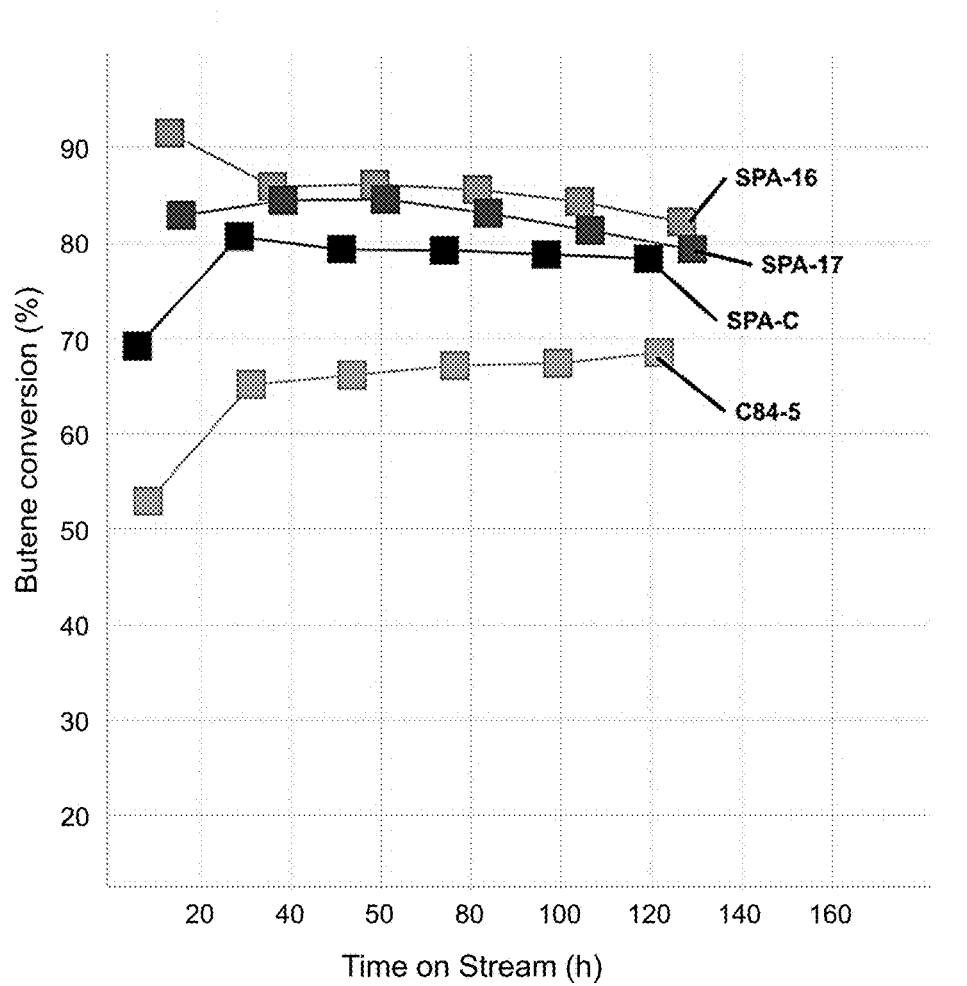
FIG. 3 is a graph of the 1-butene oligomerization performance of particular example support-modified SPA catalysts (SPA-16 and SPA-17) compared with particular comparative unmodified SPA catalysts (SPA-C and C84-5), as described in Example 4.
Figure 4:
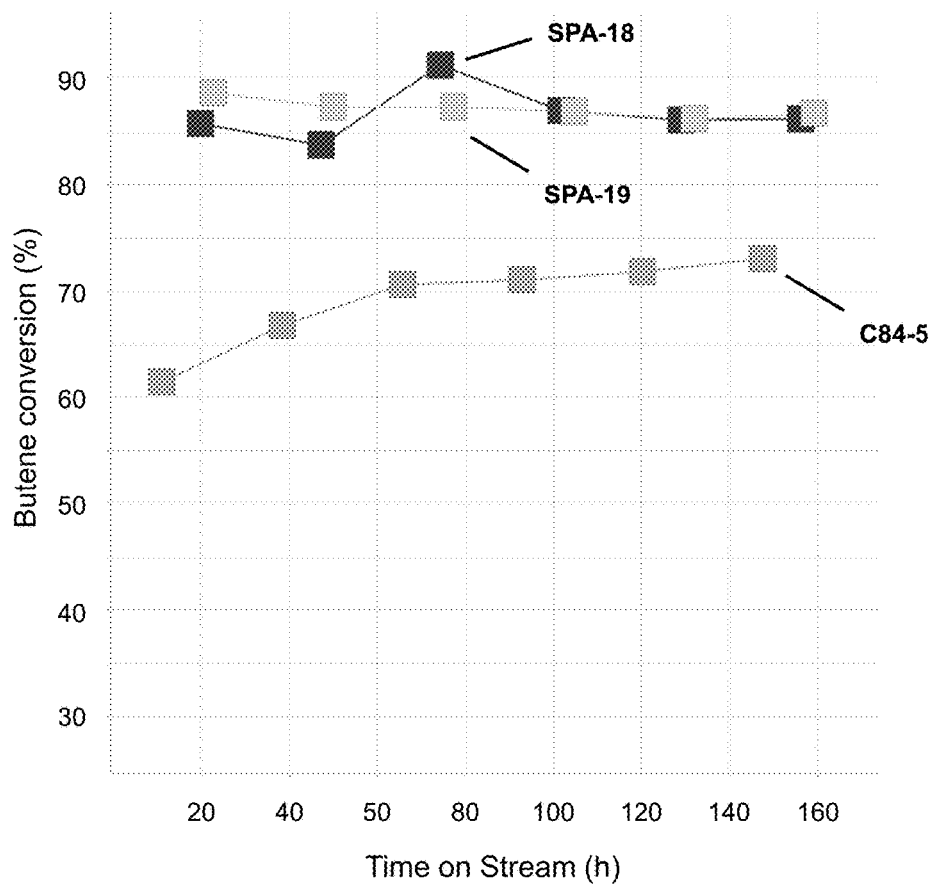
FIG. 4 is a graph of the 1-butene oligomerization performance of particular example support-modified SPA catalysts (SPA-18 and SPA-19) compared with particular comparative unmodified SPA catalysts (C84-5), as described in Example 4.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The disclosure relates to SPA catalyst compositions that include one or more phosphoric acids, one or more silicon phosphates, optionally, one or more additional inorganic phosphates; and optionally a siliceous support material. In various aspects and embodiments, a SPA catalyst composition of the disclosure (i) includes one or more promoters each selected from the group consisting of boron, bismuth, tungsten, silver and lanthanum, (ii) is a calcined product of a formable mixture that includes one or more of a silica-alumina clay, a silica fiber and a silica-alumina fiber, or (iii) is a calcined product of a formable mixture that includes fumed silica. The disclosure demonstrates such SPA catalysts to exhibit higher activity and improved stability relative to SPA catalysts lacking one or more such modifiers, such as commercially available SPA catalysts.

One aspect of the disclosure is an SPA catalyst composition. The SPA catalyst composition includes one or more phosphoric acids, one or more silicon phosphates, optionally, one or more additional inorganic phosphates, and optionally, a siliceous support material. In some aspects, the phosphoric acid may be in any oligomeric and/or polymeric state, e.g., linear phosphoric acids including orthophosphoric acid, pyrophosphoric acid, tripolyphosphoric acid, tetrapolyphosphoric acid, etc. (i.e., the $H_{n+2}P_nO_{3n+1}$ series), branched polyphosphoric acids, or metaphosphoric acids including trimetaphosphoric acid, tetrametaphosphoric acid, etc. The person of ordinary skill in the art will appreciate that in typical catalyst samples there will be a plurality of different phosphoric acids present, e.g., a mixture of two or more of the phosphoric acids specifically named above or other phosphoric acids. In some embodiments, the catalyst composition includes orthophosphoric acid and, optionally, one or more of pyrophosphoric acid, tripolyphosphoric acid, and tetrapolyphosphoric acid.

As described above, the compositions include one or more silicon phosphates. For example, in typical samples there is a significant amount of silicon phosphate(s), formed by the reaction during calcining of a phosphoric acid source and a siliceous material source. The compositions can also optionally include one or more additional inorganic phosphates, e.g., aluminum phosphates (i.e., reaction products of silica-alumina clay or silica-alumina fiber), and/or any phosphates of any other metallic components of the SPA catalyst composition, e.g., boron phosphates, bismuth phosphates, tungsten phosphates, silver phosphates, lanthanum phosphates, etc. In some aspects, such phosphates may be in any oligomeric and/or polymeric state, e.g., linear phosphates including orthophosphate, pyrophosphate, tripolyphosphate, tetrapolyphosphate, etc., branched polyphosphates, or metaphosphates. In some embodiments, the catalyst composition includes silicon orthophosphate and, optionally, one or more of silicon pyrophosphate, silicon tripolyphosphate, and silicon tetrapolyphosphate. The phosphates may be in any state of deprotonation; for example, orthophosphate may be dihydrogen phosphate ($H_2PO_4$), hydrogen phosphate ($HPO_4^{2-}$), or phosphate ($PO_4^{3-}$).

The person of ordinary skill in the art will appreciate that the ratio of silicon orthophosphate to silicon pyrophosphate may be determined from an integrated X-ray diffraction (XRD) reflectance ratio. Such a ratio is a comparison of the X-ray reflection intensities generated by the (113) planes of silicon orthophosphate and the (002) planes of silicon pyrophosphate. In some embodiments, the XRD reflectance intensity ratio of silicon orthophosphate to silicon pyrophosphate of the SPA catalyst composition is at least about 1.5:1, e.g., at least about 2:1, at least about 3:1, at least about 4:1, at least about 5:1, at least about 6:1, at least about 7:1, or at least about 8:1.

In one aspect of the compositions of the disclosure, the amount of phosphate in the calcined solid phosphoric acid catalyst composition is within the range of about 30 wt. % to about 85 wt. %, calculated as $P_2O_5$ on a calcined basis. In some embodiments of the compositions as described herein, the amount of phosphate in the calcined solid phosphoric acid catalyst composition is in the range of about 30 wt. % to about 80 wt. %, or about 30 wt. % to about 75 wt. %, or about 40 wt. % to about 85 wt. %, or about 40 wt. % to about 80 wt. %, or about 40 wt. % to about 75 wt. %, or about 45 wt. % to about 85 wt. %, or about 45 wt. % to about 80 wt. %, or about 45 wt. % to about 75 wt. %, or about 50 wt. % to about 85 wt. %, or about 50 wt. % to about 80 wt. %, or about 50 wt. % to about 75 wt. %, or about 55 wt. % to about 85 wt. %, or about 55 wt. % to about 80 wt. %, or about 55 wt. % to about 75 wt. %, or about 60 wt. % to about 85 wt. %, or about 60 wt. % to about 80 wt. %, or about 60 wt. % to about 75 wt. %, calculated as $P_2O_5$ on a calcined basis. The person of ordinary skill in the art will quantify the amount of phosphoric acid and/or inorganic phosphate using conventional methodologies in the art, e.g., XRD, pH titration and $^{31}P$ NMR. The amount of phosphoric acid can also be calculated based on the identities and amounts of materials used in making the catalyst composition. The person of ordinary skill in the art will select an amount of phosphoric acid/inorganic phosphates, together with other components, that provides the desired activity in conjunction with desired properties such as porosity and strength, based on the disclosure provided herein.

In some embodiments, the free acidity of the catalyst composition is within the range of about 10% to about 40%, e.g., about 10% to about 35%, or about 10% to about 30%, or about 10% to about 25%, or about 15% to about 40%, or about 15% to about 35%, or about 15% to about 30%, or about 15% to about 25%, or about 20% to about 40%, or about 20% to about 35%, or about 20% to about 30%, or about 20% to about 25%, calculated as $P_2O_5$. Free acidity can be determined by the person of ordinary skill in the art, for example, using pH titration.

In many embodiments, substantially no siliceous support material (i.e., other than the one or more silicon phosphates) is present in the calcined solid phosphoric acid catalyst composition. As the person of ordinary skill in the art will appreciate, in many cases the siliceous support material source in the formable mixture is converted substantially completely to silicon phosphate when the material is calcined. For example, in certain embodiments, there is less than 1 wt. %, less than 0.5 wt. % or less than 0.1 wt. % (calculated as $SiO_2$) siliceous support material (i.e., other than the one or more silicon phosphates).

However, as described above, the calcined solid phosphoric acid catalyst composition can also optionally include a siliceous support material (i.e., in addition to the silicon present as silicon phosphate). In some embodiments, the siliceous support material may be any $SiO_2$-containing material, e.g., diatomaceous earth, infusorial earth, ciliate earth, fuller's earth, kaolin, celite, artificial porous silica, etc. In some aspects, the siliceous support material may be any mixture of two or more $SiO_2$-containing materials. The person of ordinary skill in the art will appreciate that the siliceous support material can include silica-alumina clay, silica fiber, silica-alumina fiber, and/or fumed silica (all described in more detail below). In some embodiments, the siliceous support material includes diatomaceous earth. As the person of ordinary skill in the art will appreciate, the terms "diatomite", "D.E.," "kieselgur," "kieselguhr," and "guhr" are equivalent to diatomaceous earth. In certain embodiments (e.g., when no promoter selected from boron, bismuth, tungsten, silver and lanthanum is present, or when a silica-alumina clay, silica-alumina fiber and/or fumed silica is present in the formable mixture), the siliceous support material is substantially $SiO_2$, e.g., at least 90 wt. %, at least 95 wt. %, or at least 99 wt. % $SiO_2$. For example, in some embodiments (e.g., when no promoter selected from boron, bismuth, tungsten, silver and lanthanum is present, or when a silica-alumina clay, a silica fiber, a silica-alumina fiber and/or fumed silica is present) the siliceous support material includes diatomaceous earth, celite, or artificial porous silica. In some particular embodiments (e.g., when no promoter selected from boron, bismuth, tungsten, silver and lanthanum is present, or when a silica-alumina clay, a silica fiber, a silica-alumina fiber and/or fumed silica is present the formable mixture) the siliceous support material includes diatomaceous earth. Of course, the person of ordinary skill in the art will appreciate that these siliceous support materials can be present in a calcined form (i.e., as the calcined product of any such material).

In one aspect of the compositions of the disclosure, the amount of silicon in the calcined solid phosphoric acid catalyst composition is within the range of about 15 wt. % to about 85 wt. % calculated as $SiO_2$ on a calcined basis. In some embodiments, the amount of silicon in the calcined solid phosphoric acid catalyst composition is in the range of about 20 wt. % to about 70 wt. %, about 25 wt. % to about 70 wt. %, about 15 wt. % to about 60 wt. %, or about 20 wt. % to about 60 wt. %, or about 25 wt. % to about 60 wt. %, or about 15 wt. % to about 55 wt. %, or about 20 wt. % to about 55 wt. %, or about 25 wt. % to about 55 wt. %, or about 15 wt. % to about 50 wt. %, or about 20 wt. % to about 50 wt. %, or about 25 wt. % to about 50 wt. %, or about 15 wt. % to about 45 wt. %, or about 20 wt. % to about 45 wt. %, or about 25 wt. % to about 45 wt. %, or about 15 wt. % to about 40 wt. %, or about 20 wt. % to about 40 wt. %, or about 25 wt. % to about 40 wt. %, calculated as $SiO_2$ on a calcined basis. The person of ordinary skill in the art will select an amount of silicon, together with other components, that provides the desired activity in conjunction with desired properties such as porosity and strength, based on the disclosure provided herein.

The person of ordinary skill in the art will appreciate that the catalyst compositions can include a significant amount of silicon phosphates. As described above, the phosphate content will be quantified as $P_2O_5$ as described above, while the silicon content will be quantified as $SiO_2$ as described above.

In some embodiments, the atomic molar ratio of phosphorus to silicon in the SPA catalyst composition is within the range of about 0.25:1 to about 6:1, e.g., about 0.5:1 to about 6:1, or about 1:1 to 6:1, or about 2:1 to about 6:1, or about 3:1 to about 6:1, or about 4:1 to about 6:1, or about 0.25:1 to about 5:1, or about 0.5:1 to about 5:1, or about 1:1 to 5:1, or about 2:1 to about 5:1, or about 3:1 to about 5:1, or about 4:1 to about 5:1, or about 0.25:1 to about 4:1, or about 0.5:1 to about 4:1, or about 1:1 to 4:1, or about 2:1 to about 4:1, or about 3:1 to about 4:1, or about 0.25:1 to about 3:1, or about 0.5:1 to about 3:1, or about 1:1 to 3:1, or about 2:1 to about 3:1, or about 0.25:1 to about 2:1, or about 0.5:1 to about 2:1, or about 1:1 to 2:1. The person of ordinary skill in the art will select an amount of phosphoric acid/inorganic phosphates that provides the desired activity in conjunction with desired properties such as porosity and strength, based on the disclosure provided herein.

As described above, in certain embodiments of the compositions of the disclosure, the SPA catalyst composition includes one or more promoters selected from boron, bismuth, tungsten, silver, and lanthanum. For example, in one embodiment, the one or more promoters include bismuth. In other embodiments, the one or more promoters include tungsten. In other embodiments, the one or more promoters include silver. In still other embodiments, the one or more promoters include lanthanum. In certain embodiments, the one or more promoters include boron. However, in alternative embodiments, substantially no boron is present (e.g., less than about 0.01 wt. % or less than about 0.001 wt. % boron). Similarly, in alternative embodiments, substantially no tungsten is present (e.g., less than about 0.01 wt. % or less than about 0.001 wt. % boron).

The person of ordinary skill in the art will appreciate that the promoter can be present, for example, in a variety of forms, e.g., oxides, halides, silicates, phosphates, etc., or a mixture thereof. In certain embodiments, the one or more promoters are substantially present in a form selected from an oxide, a phosphate, a silicate, or a combination thereof. As described below, regardless of the actual form of the promoter species, the amount of the promoter can be calculated on an oxide basis.

In some embodiments, the promoter is present in an amount in the range of about 0.015 wt. % to about 5 wt. %, e.g., about 0.015 wt. % to about 3 wt. %, or about 0.015 wt. % to about 2 wt. %, or about 0.015 wt. % to about 1.5 wt. %, or about 0.015 wt. % to about 1 wt. %, or about 0.05 wt. % to about 0.9 wt. %, or about 0.05 wt. % to about 5 wt. %, or about 0.05 wt. % to about 3 wt. %, or about 0.05 wt. % to about 2 wt. %, or about 0.05 wt. % to about 1.5 wt. %, or about 0.05 wt. % to about 1 wt. %, or about 0.015 wt. % to about 0.9 wt. %, or about 0.1 wt. % to about 5 wt. %, or about 0.1 wt. % to about 3 wt. %, or about 0.1 wt. % to about 2 wt. %, or about 0.1 wt. % to about 1.5 wt. %, or about 0.1 wt. % to about 1 wt. %, or about 0.1 wt. % to about 0.9 wt. %, or about 0.2 wt. % to about 5 wt. %, or about 0.2 wt. % to about 3 wt. %, or about 0.2 wt. % to about 2 wt. %, or about 0.2 wt. % to about 1.5 wt. %, or about 0.2 wt. % to about 1 wt. %, or about 0.2 wt. % to about 0.9 wt. %, or about 0.5 wt. % to about 5 wt. %, or about 0.5 wt. % to about 3 wt. %, or about 0.5 wt. % to about 2 wt. %, or about 0.5 wt. % to about 1.5 wt. %, or about 0.5 wt. % to about 1 wt. %, or about 0.5 wt. % to about 0.9 wt. %, calculated as $B_2O_3$, $Bi_2O_3$, $La_2O_3$ and AgO, as appropriate.

In some embodiments, the atomic molar ratio of phosphorus to the total amount of boron, bismuth, tungsten, silver, and lanthanum in the SPA catalyst composition is within the range of about 1:0.1 to about 1:0.00005, e.g., about 1:0.075 to about 1:0.000075, or about 1:0.05 to about 1:0.0001, or about 1:0.025 to about 1:0.0002, or about 1:0.01 to about 1:0.0002, or about 1:0.0075 to about 1:0.0005, or about 1:0.005 to about 1:0.0005, or the ratio is about 1:0.0001, or about 1:0.00025 or about 1:0.0005, or about 1:0.00075, or about 1:0.001, or about 1:0.0025, or about 1:0.005, or about 1:0.0075, or about 1:0.01, or about 1:0.025, or about 1:0.05.

In some embodiments, the atomic molar ratio of silicon to the total amount of boron, bismuth, tungsten, silver, and lanthanum in the SPA catalyst composition is within the range of about 1:0.1 to about 1:0.00005, e.g., about 1:0.075 to about 1:0.000075, or about 1:0.05 to about 1:0.0001, or about 1:0.025 to about 1:0.0002, or about 1:0.01 to about 1:0.0002, or about 1:0.0075 to about 1:0.0005, or about 1:0.005 to about 1:0.0005, or the ratio is about 1:0.0001, or about 1:0.00025 or about 1:0.0005, or about 1:0.00075, or about 1:0.001, or about 1:0.0025, or about 1:0.005, or about 1:0.0075, or about 1:0.01, or about 1:0.025, or about 1:0.05.

In certain embodiments of the compositions as described herein, the total amount of the one or more phosphoric acids, the one or more silicon phosphates, the one or more (optional) inorganic phosphates, the (optional) siliceous support material, and the one or more promoters is at least about 80 wt. %, at least about 90%, at least about 95 wt. %, at least about 98 wt. %, or even at least about 99 wt. % of the catalyst composition.

In certain embodiments of the compositions of the disclosure, the calcined solid phosphoric acid catalyst composition is the calcined product of a formable mixture comprising silica-alumina clay, present in the formable mixture in an amount in the range of about 0.1 wt. % to about 15 wt. %. The silica-alumina clay can have a silica content of, for example, within the range of about 30 wt. % to about 70 wt. %, e.g., about 35 wt. % to about 65 wt. %, or about 40 wt. % to about 60 wt. %, or about 45 wt. % to about 55 wt. %, or the silica content is about 40 wt. %, or about 45 wt. %, or about 50 wt. %, or about 55 wt. %, or about 60 wt. %.

In some embodiments of the compositions as described herein, the silica-alumina clay is an aluminum phyllosilicate, e.g., halloysite, kaolinite, illite, montmorillonite, bentonite, vermiculite, talc, sepiolite, palygorksite, pyrophyllite, etc. In some embodiments, the silica-alumina clay is montmorillonite or bentonite. In some aspects, the aluminum phyllosilicate may be base-treated.

In certain embodiments of the compositions of the disclosure, the calcined solid phosphoric acid catalyst composition is the calcined product of a formable mixture comprising a silica fiber material and/or a silica-alumina fiber material, present in the formable mixture in an amount in the range of about 0.1 wt. % to about 15 wt. %. The silica/silica-alumina fiber material can have a silica content of, for example, within the range of at least about 30 wt. %, or at least about 40 wt. %, or at least about 50 wt. %, or at least about 70 wt. %, or at least about 90 wt. %, or about 30 wt. % to about 70 wt. %, e.g., about 35 wt. % to about 65 wt. %, or about 40 wt. % to about 60 wt. %, or about 45 wt. % to about 55 wt. %, or the silica content is about 40 wt. %, or about 45 wt. %, or about 50 wt. %, or about 55 wt. %, or about 60 wt. %.

In some embodiments of the compositions as described herein, the silica fiber material and/or the silica-alumina fiber material is a pure silica fiber, a chopped silica fiber, or an alumina-silica fiber of the type ASBF or ASBF-1. For example, products under the FIBERFRAX tradename, the ISOFRAX trade name, the QFIBER tradename, the EKO-WOOL trade name, and the ZIRCAR tradename can be used.

In some embodiments of the compositions as described herein, the silica-alumina clay, the silica fiber and/or silica-alumina fiber is present in the catalyst composition in an amount in the range of about 0.1 wt. % to about 15 wt. %, e.g., about 0.25 wt. % to about 15 wt. %, or about 0.5 wt. % to about 10 wt. %, or about 0.5 wt. % to about 9 wt. %, or about 0.5 wt. % to about 8 wt. %, or about 0.5 wt. % to about 7 wt. %, or about 0.5 wt. % to about 6 wt. %, or about 0.5 wt. % to about 5 wt. %, or about 2 wt. % to about 15 wt. %, or about 5 wt. % to about 15 wt. %, or about 2 wt. % to about 10 wt. %, or about 5 wt. % to about 10 wt. %, or the amount is about 0.25 wt. %, or about 0.5 wt. %, or about 0.75 wt. %, or about 1 wt. %, or about 1.25 wt. %, or about 1.5 wt. %, or about 1.75 wt. %, or about 2 wt. %, or about 3 wt. %, or about 4 wt. %, or about 5 wt. %, or about 7.5 wt. %, or about 1 wt. % on an as-calcined basis. The person of ordinary skill in the art can calculate the amount of the silica fiber and/or silica-alumina fiber, for example, based on the amounts of the materials used in the formable composition.

In some embodiments of the compositions as described above with respect to silica-alumina clays, silica fibers and silica-alumina fibers, the formable mixture further includes a siliceous support material source, and the total amount of the silica-alumina clay, the silica fiber and the silica-alumina fiber is within the range of about 0.1 wt. % to about 30 wt. % of the total amount of the siliceous support material source and the silica-alumina clay, silica fiber and/or silica-alumina fiber in the formable mixture. For example, in certain embodiments, the total amount of the silica-alumina clay, the silica-alumina fiber and/or the silica-alumina fiber is within the range of, e.g., about 0.25 wt. % to about 25 wt. %, or about 0.5 wt. % to about 20 wt. %, or about 0.75 wt. % to about 15 wt. %, or about 1 wt. % to about 10 wt. %, or about 2 wt. % to about 9 wt. %, or about 3 wt. % to about 8 wt. %, or the amount is about 0.5 wt. %, or about 1 wt. %, or about 2 wt. %, or about 3 wt. %, or about 4 wt. %, or about 5 wt. %, or about 6 wt. %, or about 7 wt. %, or about 8 wt. %, or about 9 wt. %, or about 10 wt. % of the total amount of the siliceous support material source and the silica-alumina clay, silica fiber and/or silica-alumina fiber in the formable mixture. The person of ordinary skill in the art can determine the amount of silica-alumina clay, silica fiber and/or silica- or silica-alumina fiber present in the composition conveniently from the relative amounts of raw materials used in making the catalyst compositions.

In certain embodiments, the total amount of the one or more phosphoric acids, the one or more silicon phosphates, optional aluminum phosphate (e.g., from the silica-alumina clay and/or silica-alumina fiber) and the optional siliceous support material (e.g., including silica-alumina clay, silica fiber and/or silica-alumina fiber not converted to phosphate) is at least about 80 wt. %, at least about 90%, at least about 95 wt. %, at least about 98 wt. % or even at least about 99 wt. % of the catalyst composition.

In certain embodiments of the compositions as described herein, the calcined solid phosphoric acid catalyst composition is the calcined product of a formable mixture comprising the fumed silica, present in the formable mixture in an amount within the range of about 0.1 wt. % to about 15 wt. % on a calcined basis. In some embodiments, fumed silica has at least about 90% purity, or at least about 92.5% purity, or at least about 95% purity, or at least about 96% purity, or at least about 97% purity, or at least about 98% purity, or at least about 98% purity, or at least about 98.5% purity, or at least about 99% purity, or at least about 99.5% purity, or at least about 99.9% purity. Without intending to be bound by theory, the inventors believe that addition of fumed silica in the formable mixture can enhance the orthophosphate phase, increase surface acidity, and help to provide structural stability to the catalyst.

In some embodiments of the SPA catalyst compositions as described herein, the fumed silica has a nominal particle size within the range of about 0.002 µm to about 500 µm, e.g., or about 0.002 µm to about 100 µm, or about 0.002 µm to about 50 µm, or about 0.002 µm to about 10 µm, or about 0.002 µm to about 5 µm, or about 0.002 µm to about 1 µm, or about 0.01 µm to about 500 µm, or about 0.01 µm to about 100 µm, or about 0.01 µm to about 50 µm, or about 0.01 µm to about 10 µm, or about 0.01 µm to about 5 µm, or about 0.01 µm to about 1 µm, or about 0.05 µm to about 500 µm, or about 0.05 µm to about 100 µm, or about 0.05 µm to about 50 µm, or about 0.05 µm to about 10 µm, or about 0.05 µm to about 5 µm, or about 0.05 µm to about 1 µm, or about 0.1 µm to about 500 µm, or about 0.1 µm to about 100 µm, or about 0.1 µm to about 50 µm, or about 0.1 µm to about 10 µm, or about 0.1 µm to about 5 µm, or about 0.1 µm to about 1 µm, or about 0.5 µm to about 500 µm, or about 0.5 µm to about 100 µm, or about 0.5 µm to about 50 µm, or about 0.5 µm to about 10 µm, or about 0.5 µm to about 5 µm, or about 0.5 µm to about 1 µm, or about 1 µm to about 500 µm, or about 1 µm to about 100 µm, or about 1 µm to about 50 µm, or about 1 µm to about 10 µm, or about 1 µm to about 5 µm, or about 10 µm to about 500 µm, or about 10 µm to about 100 µm, or about 10 µm to about 50 µm. Of course, the person of ordinary skill in the art will appreciate that the fumed silica is generally not present in the as-calcined material as free particles, but rather is part of the calcined mass of the catalyst material. Nonetheless, the person of ordinary skill in the art will determine the particle size of the fumed silica present in the formable mixture using conventional methodologies, or with reference to the particle size of the fumed silica raw material used.

In certain embodiments of the SPA catalyst compositions as described herein, the fumed silica has a surface area within the range of about 10 m$^2$/g to about 1000 m$^2$/g, e.g., about 25 m$^2$/g to about 900 m$^2$/g, or about 50 m$^2$/g to about 800 m$^2$/g, or about 100 m$^2$/g to about 700 m$^2$/g, or about 200 m$^2$/g to about 600 m$^2$/g, or about 300 m$^2$/g to about 500 m$^2$/g, or about 350 m$^2$/g to about 450 m$^2$/g, or about 50 m$^2$/g to about 500 m$^2$/g, or about 50 m$^2$/g to about 400 m$^2$/g, or about 50 m$^2$/g to about 300 m$^2$/g, or about 75 m$^2$/g to about 200 m$^2$/g, or about 75 m$^2$/g to about 150 m$^2$/g, or the surface area is about 25 m$^2$/g, or about 50 m$^2$/g, or about 75 m$^2$/g, or about 100 m$^2$/g, or about 125 m$^2$/g, or about 150 m$^2$/g, or about 200 m$^2$/g, or about 250 m$^2$/g, or about 300 m$^2$/g, or about 400 m$^2$/g, or about 500 m$^2$/g. The person of ordinary skill in the art will determine the surface area of the fumed silica present in the formable mixture using conventional methodologies, or with reference to the surface area of the fumed silica raw material used.

The SPA catalyst compositions described herein can be the calcined product of a formable mixture comprising fumed silica in an amount within the range of, for example, about 0.1 wt. % to about 15 wt. %. In some embodiments, the formable mixture includes a fumed silica in an amount in the range of about 0.1 wt. % to about 10 wt. %, or about 0.1 wt. % to about 5 wt. %, or about 0.1 wt. % to about 2 wt. %, or about 0.1 wt. % to about 1 wt. %, or about 0.5 wt. % to about 15 wt. %, or about 0.5 wt. % to about 10 wt. %, or about 0.5 wt. % to about 5 wt. %, or about 0.5 wt. % to about 2 wt. %, or about 0.5 wt. % to about 1 wt. %, or about 1 wt. % to about 15 wt. %, or about 1 wt. % to about 10 wt. %, or about 1 wt. % to about 5 wt. %, or about 0.5 wt. % to about 2 wt. %, or about 0.5 wt. % to about 1 wt. %.

In certain embodiments of the SPA catalyst compositions as described herein, the formable mixture includes a siliceous support material source, and the ratio of the amount of the fumed silica to the total amount of siliceous support material source and the fumed silica present in formable mixture is within the range of about 0.1 wt. % to about 30 wt. %, e.g., about 0.25 wt. % to about 25 wt. %, or about 0.5 wt. % to about 20 wt. %, or about 0.75 wt. % to about 15 wt. %, or about 1 wt. % to about 10 wt. %, or about 2 wt. % to about 9 wt. %, or about 3 wt. % to about 8 wt. %, or the amount is about 0.5 wt. %, or about 1 wt. %, or about 2 wt. %, or about 3 wt. %, or about 4 wt. %, or about 5 wt. %, or about 6 wt. %, or about 7 wt. %, or about 8 wt. %, or about 9 wt. %, or about 10 wt. %.

In certain embodiments, the total amount of the one or more phosphoric acids, the one or more silicon phosphates, and the optional siliceous support material (e.g., including any fumed silica not converted to phosphate) is at least about 80 wt. %, at least about 90 wt. %, at least about 95 wt. %, at least about 98 wt. % or at least about 99 wt. % of the catalyst composition.

The person of ordinary skill in the art will appreciate that in some cases there may be other components present in the SPA catalyst materials of the present disclosure. However, based on the disclosure herein the person of ordinary skill in the art will appreciate that effective catalysts can be made without significant amounts of other components. For example, in certain embodiments of the SPA catalyst compositions as described herein, the total amount of components other than the one or more phosphoric acids, the one or more silicon phosphates, the optional additional inorganic phosphate, and the optional siliceous support material (including any silica-alumina clay, silica fiber, silica-alumina fiber and/or fumed silica not converted to phosphate), and promoters selected from boron, bismuth, tungsten, silver and lanthanum is no more than about 15 wt. %, no more than about 10 wt. %, no more than about 5 wt. %, no more than about 2.5 wt. %, no more than about 2 wt. %, no more than about 1 wt. %, or even no more than about 0.5 wt. % of the SPA catalyst composition (measured as the most stable oxide). In certain such embodiments, there are substantially no promoters other than boron, bismuth, tungsten, silver and lanthanum present (e.g., in an amount of more than about 0.01 wt. % as the most stable oxide). In certain such embodiments, there are substantially no promoters other than bismuth, silver and lanthanum present (e.g., in an amount of more than about 0.01 wt. % as the most stable oxide). In certain such embodiments, the only additional inorganic phosphate present is a boron phosphate, a silver phosphate, a bismuth phosphate, a tungsten phosphate, a lanthanum phosphate or an aluminum phosphate.

For example, in certain embodiments, the total amount of components other than the one or more phosphoric acids, the one or more silicon phosphates, optional aluminum phosphate, and optional siliceous support material (e.g., including silica-alumina clay, silica fiber, silica-alumina fiber, and/or fumed silica not converted to phosphate at calcining) is no more than about 15 wt. %, no more than about 10 wt. %, no more than about 5 wt. %, no more than about 2.5 wt. %, no more than about 2 wt. %, no more than about 1 wt. %, or even no more than about 0.5 wt. % of the SPA catalyst composition (measured as the most stable oxide). In certain such embodiments, there are substantially no promoters present (e.g., in an amount of more than about 0.01 wt. % as the most stable oxide).

In certain embodiments of the SPA catalyst compositions as described herein, the total amount of components other than the one or more phosphoric acids, the one or more silicon phosphates, the optional siliceous support material, and promoters selected from boron, bismuth, tungsten, silver and lanthanum (e.g., in any form, including phosphate or oxide), is no more than about 15 wt. %, no more than about 10 wt. %, no more than about 5 wt. %, no more than about 2.5 wt. %, no more than about 2 wt. %, no more than about 1 wt. %, or even no more than about 0.5 wt. % of the SPA catalyst composition (measured as the most stable oxide). In certain such embodiments, there is substantially no silica-alumina clay, silica fiber or silica-alumina fiber present in the formable mixture calcined to make the composition (e.g., in an amount more than 0.1 wt. %). In certain such embodiments, there is substantially no fumed silica present in the formable mixture calcined to make the composition (e.g., in an amount more than 0.1 wt. %). In certain such embodiments, there are substantially no promoters other than boron, bismuth, tungsten, silver and lanthanum present (e.g., in an amount of more than about 0.01 wt. % as the most stable oxide). In certain such embodiments, there are substantially no promoters other than bismuth, silver and lanthanum present (e.g., in an amount of more than about 0.01 wt. % as the most stable oxide).

In certain embodiments of the SPA catalyst compositions as described herein, the total amount of components other than the one or more phosphoric acids, the one or more silicon phosphates, the optional siliceous support material, and promoters selected from boron, bismuth, tungsten, silver and lanthanum is no more than about 15 wt. %, no more than about 10 wt. %, no more than about 5 wt. %, no more than about 2.5 wt. %, no more than about 2 wt. %, no more than about 1 wt. %, or even no more than about 0.5 wt. % of the SPA catalyst composition (measured as the most stable oxide). In certain such embodiments, there is substantially no fumed silica, silica fiber, silica-alumina clay or silica-alumina fiber present (e.g., in an amount more than 0.1 wt. %) in the formable mixture calcined to make the composition. In certain such embodiments, there are substantially no promoters other than boron, bismuth, tungsten, silver and lanthanum present (e.g., in an amount of more than about 0.01 wt. % as the most stable oxide). In certain such embodiments, there are substantially no promoters other than bismuth, tungsten, silver and lanthanum present (e.g., in an amount of more than about 0.01 wt. % as the most stable oxide).

For example, in certain embodiments, the total amount of components other than the one or more phosphoric acids, the silicon phosphate, and the optional siliceous support material (including any fumed silica not converted to phosphate) is no more than about 15 wt. %, no more than about 10 wt. %, no more than about 5 wt. %, no more than about 2.5 wt. %, no more than about 2 wt. %, no more than about 1 wt. %, or even no more than about 0.5 wt. % of the SPA catalyst composition (measured as the most stable oxide). In certain such embodiments, there are substantially no promoters present (e.g., in an amount of more than about 0.01 wt. % as the most stable oxide). In certain such embodiments, there is substantially no silica fiber, silica-alumina clay and/or silica-alumina fiber present (e.g., in an amount of more than about 0.1 wt. %) in the formable mixture calcined to make the catalyst composition.

For example, in certain embodiments, the total amount of components other than the one or more phosphoric acids, the silicon phosphate, optional aluminum phosphate, and the optional siliceous support material (including any silica fiber, silica-alumina fiber or silica-alumina clay not converted to phosphate) is no more than about 15 wt. %, no more than about 10 wt. %, no more than about 5 wt. %, no more than about 2.5 wt. %, no more than about 2 wt. %, no more than about 1 wt. %, or even no more than about 0.5 wt. % of the SPA catalyst composition (measured as the most stable oxide). In certain such embodiments, there are substantially no promoters present (e.g., in an amount of more than about 0.01 wt. % as the most stable oxide). In certain such embodiments, there is substantially no fumed silica present (e.g., in an amount of more than about 0.1 wt. %) in the formable mixture calcined to make the catalyst composition.

As noted above, the SPA catalyst compositions described herein are in the form of a calcined extrudate. The person of ordinary skill in the art will appreciate that the amounts of material in the calcined extrudate are to be calculated on an as-calcined, basis, exclusive of any organic material and any adsorbed water.

Another aspect of the disclosure is a method of preparing a calcined SPA catalyst composition, such as those described herein. The method includes providing a formable mixture comprising a phosphate source present in an amount within the range of about 30 wt. % to about 85 wt. % on a calcined weight basis (as $P_2O_5$), a siliceous support material source present in an amount within the range of about 15 wt. % to about 70 wt. % on a calcined weight basis (as $SiO_2$), and at least one of (i) one or more promoters each selected from the group consisting of boron, bismuth, tungsten, silver and lanthanum, present in an amount within the range of about 0.015 wt. % to about 5 wt. % on a calcined weight basis (as $B_2O_3$, $Bi_2O_3$, AgO or $La_2O_3$); (ii) a silica-alumina clay, a silica fiber and/or an alumina-silica fiber, present in an amount within the range of about 0.1 wt. % to about 15 wt. % on a calcined weight basis (as $SiO_2/Al_2O_3$); and (iii) fumed silica present in an amount within the range of about 0.1 wt. % to about 15 wt. % on a calcined weight basis (as $SiO_2$). The method includes forming (e.g., by extruding, tableting or pelletizing) the mixture and calcining the formed mixture.

The amounts of material in the formable mixture are calculated on a calcined weight basis. Accordingly, the amounts of source materials described herein with respect to the components of the formable mixture correspond to the amounts of the components of the calcined extrudate compositions described above. The person of ordinary skill in the art will appreciate that any of the amounts component described above with respect to the catalyst compositions described above can be directly used numerically as the amount of the corresponding source material in the formable mixture.

The formable mixture includes a phosphate source. In some aspects, the phosphate source may be phosphoric acid, a compound that forms phosphoric acid by hydrolysis, or any mixture thereof. In some aspects, the phosphoric acid may be in any oligomeric and/or polymeric state, e.g., linear phosphoric acids including orthophosphoric acid, pyrophosphoric acid, tripolyphosphoric acid, tetrapolyphosphoric acid, etc. (i.e., the $H_{n+2}P_nO_{3n+1}$ series), branched polyphosphoric acids, or metaphosphoric acids including trimetaphosphoric acid, tetrametaphosphoric acid, etc. In some aspects, free phosphoric acidic sites comprising the catalyst precursor material (i.e., Bronsted sites) may be deprotonated. For example, orthophosphoric acid may be present as phosphoric acid ($H_3PO_4$) or as one of the conjugate bases dihydrogen phosphate ($H_2PO_4^-$), hydrogen phosphate ($HPO_4^{2-}$), or phosphate ($PO_4^{3-}$). In some embodiments, the catalyst precursor material includes orthophosphoric acid and, optionally, one or more of pyrophosphoric acid, tripolyphosphoric acid, and tetrapolyphosphoric acid.

In some embodiments, the phosphate source contains linear phosphoric acids and water. The person of ordinary skill in the art will appreciate that this mixture is characterized by the total phosphorus content, which is given as a percentage relative to pure orthophosphoric acid, $H_3PO_4$. As the other acids in the linear phosphoric acid series (i.e., $H_{n+2}P_nO_{3n+1}$) have a higher phosphorus content by weight than orthophosphoric acid, it is not unusual to find phosphoric acids with concentration greater than 100%. In some embodiments, the phosphate source is phosphoric acid with a concentration within the range of about 90% to about 130%, e.g., about 95% to about 125%, or about 100% to about 120%, or about 105% to about 115%, or the concentration is about 100%, or about 105%, or about 110%, or about 115%, or about 120%.

In some embodiments, the formable mixture material includes a phosphate source present in an amount in the range of 30 wt. % to about 85 wt. % on a calcined weight basis, calculated as $P_2O_5$. In some embodiments of the methods as described herein, the catalyst composition includes a phosphate source present in an amount in the range of about 30 wt. % to about 80 wt. %, or about 30 wt. % to about 75 wt. %, or about 40 wt. % to about 85 wt. %, or about 40 wt. % to about 80 wt. %, or about 40 wt. % to about 75 wt. %, or about 45 wt. % to about 85 wt. %, or about 45 wt. % to about 80 wt. %, or about 45 wt. % to about 75 wt. %, or about 50 wt. % to about 85 wt. %, or about 50 wt. % to about 80 wt. %, or about 50 wt. % to about 75 wt. %, or about 55 wt. % to about 85 wt. %, or about 55 wt. % to about 80 wt. %, or about 55 wt. % to about 75 wt. %, or about 60 wt. % to about 85 wt. %, or about 60 wt. % to about 80 wt. %, or about 60 wt. % to about 75 wt. %, of about 30 wt. % to about 95 wt. %, e.g., about 35 wt. % to about 90 wt. %, or about 40 wt. % to about 90 wt. %, or about 45 wt. % to about 90 wt. %, or about 50 wt. % to about 85 wt. %, or about 55 wt. % to about 80 wt. %, or about 60 wt. % to about 75 wt. %, or about 65 wt. % to about 75 wt. %, or in an amount of about 50 wt. %, or about 55 wt. %, or about 60 wt. %, or about 65 wt. %, or about 70 wt. %, or about 75 wt. %, or about 80 wt. %, or about 85 wt. %, on an calcined weight basis calculated as $P_2O_5$ (i.e., based on the total phosphorus content).

The formable mixture also includes a siliceous support material source. The siliceous support material source may be as described herein with respect to the catalyst compositions. In some embodiments, the siliceous support material may be any $SiO_2$-containing material, e.g., diatomaceous earth, infusorial earth, ciliate earth, fuller's earth, kaolin, celite, artificial porous silica, etc. In some aspects, the siliceous support material source may be any mixture of two or more $SiO_2$-containing materials. In some embodiments, the siliceous support material source is diatomaceous earth. In certain embodiments (e.g., when no promoter selected from boron, bismuth, tungsten, silver and lanthanum is present, or when a silica-alumina clay, silica fiber, silica-alumina fiber and/or fumed silica is present), the siliceous support material source is substantially $SiO_2$, e.g., at least 90 wt. %, at least 95 wt. %, or at least 99 wt. % $SiO_2$. For example, in some embodiments (e.g., when no promoter selected from boron, bismuth, tungsten, silver and lanthanum is present, or when a silica-alumina clay, silica fiber, silica-alumina fiber and/or fumed silica is present) the siliceous support material source is diatomaceous earth, celite, artificial porous silica, or diatomaceous earth. In some particular embodiments (e.g., when no promoter selected from boron, bismuth, tungsten, silver and lanthanum is present, or when a silica-alumina clay, silica fiber, silica-alumina fiber and/or fumed silica is present) the siliceous support material source is diatomaceous earth.

In some embodiments, the formable mixture includes a siliceous support material source present in amount within the range of about 15 wt. % to about 85 wt. %. In some embodiments, the formable material includes a siliceous support material present in an amount in the range of about 20 wt. % to about 70 wt. %, about 25 wt. % to about 70 wt. %, or about 15 wt. % to about 60 wt. %, or about 20 wt. % to about 60 wt. %, or about 25 wt. % to about 60 wt. %, or about 15 wt. % to about 55 wt. %, or about 20 wt. % to about 55 wt. %, or about 25 wt. % to about 55 wt. %, or about 15 wt. % to about 50 wt. %, or about 20 wt. % to about 50 wt. %, or about 25 wt. % to about 50 wt. %, or about 15 wt. % to about 45 wt. %, or about 20 wt. % to about 45 wt. %, or about 25 wt. % to about 45 wt. %, or about 15 wt. % to about 40 wt. %, or about 20 wt. % to about 40 wt. %, or about 25 wt. % to about 40 wt. %, calculated as $SiO_2$.

In some embodiments, the atomic molar ratio of phosphorus to silicon in the formable mixture is within the range of about 0.25:1 to about 6:1, e.g., about 0.5:1 to about 5.5:1, or about 1:1 to about 5:1, or about 1.5:1 to about 4.5:1, or about 2:1 to about 4:1, or about 2.5:1 to about 3.5:1, or the ratio is about 1:1, or about 1.5:1, or about 2:1, or about 2.5:1, or about 3:1, or about 3.5:1, or about 4:1, or about 4.5:1, or about 5:1.

In certain embodiments, the formable mixture includes one or more sources of one or more promoters selected from boron, bismuth, tungsten, silver, and lanthanum. In some aspects, the promoter maybe any mixture of two or more of boron, bismuth, tungsten, silver, and lanthanum. The person of ordinary skill in the art will appreciate that the source of promoter can be present in the formable material in a variety of forms, e.g., acids, oxides, halides, phosphates, silicates, acetates, etc.; these will typically be converted to oxide, silicate, phosphate and/or aluminate forms during calcining. In some aspects, the source of promoter may be present in a combination or two or more forms. The amount of promoter in the formable mixture can be the same as described above with respect to the catalyst compositions.

For example, in certain embodiments, a water-soluble boron-containing compound can be used as a source for boron as a promoter in the catalyst material. The water solubility of the water-soluble boron-containing compound is, in certain desirable embodiments, at least 0.1 g/L, at least 1 g/L, or even at least 5 g/L at 25° C. (i.e., at any pH in the range of 3-10). The water-soluble boron-containing compound can be, for example, boric acid or boron trioxide. In certain desirable embodiments, use of a water-soluble boron-containing compound as a source can provide much more homogeneous doping of boron than other sources, thereby allowing a lower overall level of doping.

Similarly, in certain embodiments, a water-soluble tungsten-containing compound can be used as a source for tungsten as a promoter in the catalyst material. The water solubility of the water-soluble tungsten-containing compound is, in certain desirable embodiments, at least 0.1 g/L, at least 1 g/L, or even at least 5 g/L at 25° C. (i.e., at any pH in the range of 3-10). The water-soluble tungsten-containing compound can be, for example, a heteropolytungstate, e.g., a silicotungstate such as silicotungstic acid, or a phosphotungstate such as phosphotungstic acid. Other water-soluble tungsten-containing compounds include tungstic acid, ammonium metatungstate and ammonium paratungstate. In certain desirable embodiments, use of a water-soluble tungsten-containing compound as a source can provide much more homogeneous doping of tungsten than other sources, thereby allowing a lower overall level of doping.

Water soluble promoter sources can also be useful with respect to any promoter described herein. For example, in certain embodiments, the sources of the one or promoters have water solubilities of at least 0.1 g/L, at least 1 g/L, or even at least 5 g/L at 25° C. (i.e., at any pH in the range of 3-10).

In certain embodiments, the formable mixture includes a silica-alumina clay, a silica fiber and/or a silica-alumina fiber. The identities and amounts of silica-alumina clay, silica fiber and/or silica-alumina fiber in the formable mixture can be the same as described above with respect to the catalyst compositions. But in other embodiments, the formable mixture does not substantially include a silica-alumina clay, a silica fiber and/or a silica-alumina fiber, as described above.

The person of ordinary skill in the art will appreciate that the forms of the phosphate source, siliceous support material source, and the promoter(s), silica-alumina clay, silica fiber, silica-alumina fiber and fumed silica (together, "modifiers") in the formable material may be varied and combined in a number of ways.

The person of ordinary skill in the art will also appreciate that the order of addition of the phosphate source, siliceous support material, and one or more modifiers to the formable mixture may vary in a number of ways. In one example, the phosphate source and siliceous support material are mixed together before the one or more modifiers are added. In another example, the phosphate source and the one or more modifiers are mixed together before the siliceous support material source is added. In another example, the siliceous support material source and the one or more modifiers are mixed together before the phosphate source is added.

The person of ordinary skill in the art will appreciate that other conventional materials can be included in the formable mixture, e.g., water, binders, cements, or any other materials to aid with mixing or forming (e.g., via extrusion).

The catalyst precursor material may be mixed by a variety of methods, both manual and mechanical. In some embodiments, two or more components of the formable mixture are mixed by hand. In some embodiments, two or more components of the formable mixture are mixed mechanically. In some aspects, the mechanical mixing may be accomplished using, e.g., a planetary mixer, a spiral mixer, a stand mixer, screw extruder etc. In some embodiments, the formable mixture may be mixed by a combination of hand and mechanical mixing. In one example, the phosphate source and one or more modifiers are mixed by hand before the siliceous support material is added. The formable mixture is then mixed again, first by hand and second mechanically.

The method of preparing an SPA catalyst composition may optionally include a precalcining step before the formable mixture is formed. As used herein, the term "precalcine" describes the first calcination step in a process in which there are at least two calcination steps (i.e., a material may be precalcined, then calcined). In some aspects, the precalcination step may be performed at a temperature lower than that of the calcination step. In some embodiments, the formable mixture comprising the phosphate source, siliceous support material, and one or more modifiers is precalcined before it is formed. In some embodiments, the formable mixture is precalcined at a temperature within the range of about 50° C. to about 350° C., e.g., about 75° C. to about 325° C., or about 100° C. to about 300° C., or about 125° C. to about 275° C., or about 150° C. to about 250° C., or about 175° C. to about 225° C., or the temperature is about 100° C., or about 125° C., or about 150° C., or about 175° C., or about 200° C., or about 225° C., or about 250° C., or about 275° C., or about 300° C.

In some embodiments, the formable mixture is precalcined for a period of time within the range of 5 min. to about 2 hr., e.g., about 5 min. to about 1.5 hr., or about 5 min. to about 1 hr., or about 5 min. to about 50 min., or about 5 min. to about 35 min., or about 10 min. to about 30 min., or about 15 min. to about 25 min., or the period of time is about 5 min., or about 10 min., or about 15 min., or about 20 min., or about 25 min., or about 30 min., or about 35 min., or about 40 min., or about 45 min.

After a precalcining step, it will typically be desirable to rehydrate the mixture in order to ensure it is formable for the forming step. Organic binders and extrusion aids can be advantageously added after precalcining.

It is advantageous to add a material which produces gases during calcination, as this aids in the formation of the large pores which characterize this catalyst. Materials which produce gases during calcination include, without limitation, materials such as water or other volatiles which produce gas by evaporation or loss on ignition, and organic or inorganic materials such as those containing starch, cellulose, nitrates, carbonates, oxalates, acetates or other organic salts, polymers, or compounds containing coordinated water or ammonia, which produce gas by decomposition or combustion. In certain embodiments, a pore-forming organic material (e.g., polyethylene glycol) is added to the precalcined mixture before forming the catalyst composition. The pore-forming organic material can be burned away during the calcining step, leaving pores behind. The use of pore-forming organic materials is familiar to the person of ordinary skill in the art.

The method of preparing an SPA catalyst composition includes forming the optionally precalcined formable mixture. The person of ordinary skill in the art will appreciate that the optionally precalcined formable mixture may be formed into a variety of shapes, e.g., extrudates, pellets, tablets, spheres, etc. A variety of means for forming such shapes are known in the art, e.g., extrusion, pelletizing, marumarizing, etc. In some embodiments, the formable mixture is formed by extrusion into an extrudate. The person of ordinary skill in the art will select extrusion conditions to provide desired pore volumes.

The method of preparing an SPA catalyst composition also includes calcining the formed mixture. In some aspects, the calcination step may be performed at a temperature higher than that of the precalcination step. In some embodiments, the formed catalyst precursor material is calcined at a temperature within the range of about 120° C. to about 520° C., e.g., about 150° C. to about 490° C., or about 180° C. to about 460° C., or about 210° C. to about 430° C., or about 240° C. to about 400° C., or about 260° C. to about 380° C., or about 280° C. to about 360° C., or about 300° C. to about 340° C., or the temperature is about 240° C., or about 260° C., or about 280° C., or about 300° C., or about 320° C., or about 340° C., or about 360° C., or about 380° C., or about 400° C.

In some embodiments, the formed catalyst precursor material is calcined for a period of time within the range of 5 min. to about 2.5 hr., e.g., about 5 min. to about 2 hr., or about 5 min. to about 1.5 hr., or about 5 min. to about 1 hr., or about 5 min. to about 55 min., or about 10 min. to about 50 min., or about 15 min. to about 45 min., or about 20 min. to about 40 min., or about 25 min. to about 35 min., or the period of time is about 10 min., or about 15 min., or about 20 min., or about 25 min., or about 30 min., or about 35 min., or about 40 min., or about 45 min., or about 50 min.

The person of ordinary skill in the art will select calcination conditions, including, possibly, multiple calcination steps at different times, temperatures, oxygen levels and moisture levels, to provide the desired material. The formed mixture may be calcined in two or more stages, with each stage having its own time, temperature, oxygen level, and moisture level. For example, the extrudates may be dried at 120° C. for 1 hour in dry air, calcined at 400° C. for 1.5 hours in dry air, and then steamed at 200° C. for 0.5 hours in a 4:1 mixture of air and steam. However, it is not necessary to employ multiple calcination stages: a single stage in which the extrudates are held at a constant temperature for a certain amount of time may also be used.

The initial, "green" formed mixture is typically amorphous, and must undergo crystallization to produce the finished catalyst. Crystallization can occur in the period between mixing the ingredients and forming, in the period between forming and calcination, and during calcination.

The calcination temperature and calcination time should be sufficient to ensure growth of the crystalline phases of silicon orthophosphate and silicon pyrophosphate and the desired pore characteristics. Calcination temperatures above 500° C. contribute to excessive formation of silicon pyrophosphate and insufficient formation of silicon orthophosphate. In order to obtain a mixture of silicon orthophosphate and silicon pyrophosphate, the calcination temperature (or highest calcination temperature, if there are multiple calcination stages) should be in the range between about 200° C. and about 500° C., preferably between about 350° C. and about 450° C. Calcination times (total times, if there is more than one calcination stage) will vary depending on other calcination factors, but calcination times between about 20 minutes and about 4 hours are preferred.

In some embodiments, the method of preparing an SPA catalyst composition also includes a step of surface coating the calcined SPA catalyst composition. In some aspects, the calcined SPA catalyst may be surface coated with any SiO$_2$-containing material, e.g., diatomaceous earth, infusorial earth, ciliate earth, fuller's earth, kaolin, celite, artificial porous silica, etc. In some embodiments, the calcined SPA catalyst is surface coated with diatomaceous earth.

Another aspect of the disclosure is a catalyst composition made by a method as described herein.

Another embodiment of the disclosure is a method of converting hydrocarbons. The method includes providing a SPA catalyst composition as described herein. The method also includes contacting a hydrocarbon feed with the provided SPA catalyst composition. In some aspects, the hydrocarbon conversion may be oligomerization of an olefin, e.g., propylene oligomerization, butene oligomerization, etc. In some aspects, the hydrocarbon conversion may be alkylation of an aromatic hydrocarbon, e.g., benzene alkylation, etc. In some embodiments, the hydrocarbon conversion is olefin oligomerization.

The catalyst compositions of the present disclosure may be used, for example, in the alkylation of aromatic hydrocarbons with olefins to produce alkyl aromatics. In one embodiment, benzene is reacted with ethylene to produce ethylbenzene. In another embodiment, benzene is reacted with propylene to produce cumene. In a typical process, the aromatic hydrocarbon and the olefin are continuously fed into a pressure vessel containing the solid phosphoric acid catalyst of this disclosure. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably-from about 2:1 to 8:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor. A controlled amount of water, in quantities between about 0.01% and about 6% of the combined aromatic and olefin feed, is preferably added to the alkylation reaction zone, in order to prevent dehydration of the catalyst, which affects catalyst performance.

The catalyst compositions of the present disclosure may also be used in a polygas process. In this process, sometimes called catalytic condensation, olefins in the feed stream are oligomerized to produce heavier hydrocarbons. In an exemplary embodiment, the particles of the catalyst are placed in vertical cylindrical treating towers or in fixed beds in reactors or towers and the gases containing olefins are passed downwardly through the reactors or towers at temperatures of 170° C. to 290° C. and pressures of 6 to 102 atmospheres. These conditions are particularly applicable when dealing with olefin-containing material which may contain from approximately 10 to 50 percent or more of propylene and butylenes. When operating on a mixture comprising essentially propylene and butylenes, preferred process conditions are a temperature from about 140° C. to about 250° C., and at a pressure of from about 34 to about 102 atmospheres.

In some aspects, the hydrocarbon feed may include any C3 or C4 hydrocarbon. In some aspects, the hydrocarbon may include saturated or unsaturated (i.e., olefinic) hydrocarbons. As the person of ordinary skill in the art will appreciate, the hydrocarbon feed may include a number of combinations of C3 and C4 hydrocarbons, and a number of combinations of saturated and olefinic hydrocarbons. In some embodiments, the hydrocarbon feed includes propylene. In some embodiments, the hydrocarbon feed includes 1-butene.

In some embodiments, the hydrocarbon feed includes an olefinic hydrocarbon present in an amount within the range of about 5 wt. % to about 95 wt. %, e.g., about 10 wt. % to about 90 wt. %, or about 15 wt. % to about 85 wt. %, or about 20 wt. % to about 80 wt. %, or about 20 wt. % to about 70 wt. %, or about 20 wt. % to about 60 wt. %, or about 20 wt. % to about 50 wt. %, or about 20 wt. % to about 40 wt. %, or about 30 wt. % to about 80 wt. %, or about 35 wt. % to about 75 wt. %, or about 40 wt. % to about 70 wt. %, or about 45 wt. % to about 65 wt. %, or the amount is about 15 wt. %, or about 20 wt. %, or about 25 wt. %, or about 30 wt. %, or about 35 wt. %, or about 40 wt. %, or about 45 wt. %, or about 50 wt. %, or about 55 wt. %, or about 60 wt. %, or about 65 wt. %, or about 70 wt. %.

In some embodiments, the hydration level of the hydrocarbon feed is within the range of about 50 ppm to about 1000 ppm, e.g., about 100 ppm to about 900 ppm, or about 150 ppm to about 850 ppm, or about 200 ppm to about 800 ppm, or about 250 ppm to about 750 ppm, or about 300 ppm to about 700 ppm, or about 350 ppm to about 650 ppm, or about 400 ppm to about 600 ppm, or about 450 ppm to about 550 ppm, or the hydration level is about 200 ppm, or about 250 ppm, or about 300 ppm, or about 350 ppm, or about 400 ppm, or about 450 ppm, or about 500 ppm, or about 550 ppm, or about 600 ppm, or about 650 ppm, or about 700 ppm.

In some embodiments, the hydrocarbon is contacted with the provided SPA catalyst composition at a liquid hourly space velocity of about 0.1 h$^{-1}$ to about 5 h$^{-1}$, e.g., about 0.25 h$^{-1}$ to about 4.5 h$^{-1}$, or about 0.5 h$^{-1}$ to about 4 h$^{-1}$, or about 0.75 h$^{-1}$ to about 3.5 h$^{-1}$, or about 1 h$^{-1}$ to about 3 h$^{-1}$, or about 1 h$^{-1}$ to about 2.5 h$^{-1}$, or about 1 h$^{-1}$ to about 2 h$^{-1}$, or about 1 h$^{-1}$ to about 1.75 h$^{-1}$, or about 1 h$^{-1}$ to about 1.5 h$^{-1}$, or the liquid hourly space velocity is about 0.25 h$^{-1}$, or about 0.5 h$^{-1}$, or about 0.75 h$^{-1}$, or about 1 h$^{-1}$, or about 1.25 h$^{-1}$, or about 1.5 h$^{-1}$, or about 1.75 h$^{-1}$, or about 2 h$^{-1}$, or about 2.5 h$^{-1}$, or about 3 h$^{-1}$, or about 3.5 h$^{-1}$, or about 4 h$^{-1}$.

In some embodiments, the method of converting hydrocarbons is carried out at a temperature within the range of about 50° C. to about 450° C., e.g., about 75° C. to about 400° C., or about 100° C. to about 350° C., or about 100° C. to about 300° C., or about 100° C. to about 250° C., or about 100° C. to about 200° C., or about 125° C. to about 175° C., or the temperature is about 100° C., or about 120° C., or about 140° C., or about 160° C., or about 180° C., or about 200° C., or about 220° C., or about 240° C., or about 260° C., or about 280° C., or about 300° C.

In some embodiments, the method of converting hydrocarbons is carried out at a pressure within the range of about 1 bar to about 150 bars, e.g., about 5 bars to about 125 bars, or about 5 bars to about 100 bars, or about 5 bars to about 90 bars, or about 10 bars to about 80 bars, or about 15 bars to about 70 bars, or about 20 bars to about 60 bars, or about 25 bars to about 50 bars, or about 30 bars to about 45 bars, or about 35 bars to about 40 bars, or the pressure is about 15 bars, or about 20 bars, or about 25 bars, or about 30 bars, or about 35 bars, or about 40 bars, or about 45 bars, or about 50 bars, or about 55 bars, or about 60 bars, or about 65 bars, or about 70 bars.

EXAMPLES

The Examples that follow are illustrative of specific embodiments of the invention, and various uses thereof. They are set forth for explanatory purposes only, and are not to be taken as limiting the invention.

Example 1

SPA Catalyst Synthesis 100 g phosphoric acid (113% concentration) at 45° C. was added to a mixing bowl. 39 g diatomaceous earth (CELATOM® MN-2) was then added to the bowl and mixed first by hand, then mechanically at high speed for 1-2 min. The mixture was transferred to a crystallization dish and precalcined in air at 200° C. for 20 min. The mixture was allowed to cool to room temperature (RT) over 10 minutes, then extruded using a hydraulic press (Carver, Inc.) at a pressure of 18-20 kPsi. The extrudate was calcined in air at 320° C. for 30 min., providing unmodified SPA catalyst "SPA-C"

Example 2

Promoter-Modified SPA Catalyst Synthesis 100 g phosphoric acid (113% concentration) at 45° C. was added to a mixing bowl. A promoter reagent was then added according to Table 1 and mixed with the phosphoric acid 39 g diatomaceous earth (CELATOM® MN-2) was added to the bowl and mixed with the acid and promoter first by hand, then mechanically at high speed for 1-2 min. The mixture was transferred to a crystallization dish and precalcined in air at 200° C. for 20 min. The mixture was allowed to cool to room temperature (RT) over 10 min., then extruded using a hydraulic press (Carver, Inc.) at a pressure according to Table 1. The extrudate was calcined in air at 320° C. for 30 min.

TABLE 1

Promoter-Modified SPA Catalysts

| Catalyst | Promoter | Promoter Reagent | Reagent Amount (g) | Extrusion Pressure (kPsi) | Promoter Amount (wt. %)[1] |
|---|---|---|---|---|---|
| SPA-1 | Boron | Boric Acid | 0.8 | 18-20 kPsi | 0.4 |
| SPA-2 | Bismuth | Bismuth(III) Acetate | 0.65 | 12-15 kPsi | 0.9 |
| SPA-3 | Lanthanum | Lanthanum(III) Acetate Hydrate | 0.80 | 12-15 kPsi | 0.9 |
| SPA-4 | Silver | Silver(I) Acetate | 0.54 | 12-15 kPsi | 0.9 |

[1]Calculated as percentage of combined promoter and siliceous support material

Example 3

Support-Modified SPA Catalyst Synthesis 100 g phosphoric acid (113% concentration) at 45° C. was added to a mixing bowl. 2 g of a support modifier according to Table 2 was added and mixed by hand with the phosphoric acid. 37 g diatomaceous earth (CELATOM® MN-2) was added to the bowl and mixed with the acid and support modifier first by hand, then mechanically at high speed for 1-2 min. The mixture was transferred to a crystallization dish and precalcined in air at 200° C. for 20 min. The mixture was allowed to cool to room temperature (RT) over 10 min., then extruded using a hydraulic press (Carver, Inc.) at a pressure according to Table 2. The extrudate was calcined in air at 320° C. for 30 min. The calcined extrudate contained 5% support modifier relative to the combined amount of siliceous support material (in this Example, diatomaceous earth) and support modifier.

TABLE 2

Support-Modified SPA Catalysts

| Catalyst | Support Modifier (SM) | SM Material | SM Particle Size (μM) | SM Surface Area (m$^2$/g) | SM % SiO$_2$ | Extrusion Pressure (kPsi) |
|---|---|---|---|---|---|---|
| SPA-5 | FIBERFRAX ® PS 3400 | Silica Fiber | 1-2 | | 48-53 | 18-20 |
| SPA-6 | CARIACT ® Q50 | Fumed Silica | ~0.5 | ~100 | >99.8 | 20-22 |
| SPA-7 | HDK ® C10 Silica | Fumed Silica | 0.3 | 80-120 | >99.8 | 18-20 |
| SPA-8 | AEROSIL ® 200 | Fumed Silica | 12 | 80-120 | >99.8 | 15-18 |
| SPA-9 | ULTRASIL ® 360 | Fumed Silica | 0.38 | 55 | >99.8 | 15-18 |
| SPA-10 | Sigma-Aldrich S5130 | Fumed Silica | 0.007 | 370-420 | >99.8 | 15-18 |
| SPA-11 | CAB-O-SIL ® LM150D | Fumed Silica | 0.6 | 200 | 97 | 12-14 |
| SPA-12 | Alfa Aesar 42756 | Fumed Silica | 2 | 85-115 | 97 | 12-15 |
| SPA-13 | SYLOPOL ® 952 | Fumed Silica | 33 | 270 | 97 | 15-17 |
| SPA-14 | SIPERNAT ® 22 | Fumed Silica | 115 | 180 | 97 | 15-17 |
| SPA-15 | Montmorillonite K 10 | Aluminum Phyllosilicate | <63 (75%) | 220-270 | 73 | 20-22 |
| SPA-16 | TONSIL ® Supreme | Aluminum Phyllosilicate | | | | 15-17 |
| SPA-17 | Base-Treated TONSIL ® Supreme | Aluminum Phyllosilicate | | | | 15-17 |

[1]Calculated as percentage of combined support modifier and siliceous support material

Example 4

Tungsten-Modified SPA Catalyst Synthesis 100 g phosphoric acid (113% concentration) at 45° C. was added to a mixing bowl. A tungsten promoter reagent was then added according to Table 3 and mixed by hand with the phosphoric acid. 39 g diatomaceous earth (CELATOM® MN-2) was added to the bowl and mixed with the acid and promoter first by hand, then mechanically at high speed for 1-2 min. The mixture was transferred to a crystallization dish and precalcined in air at 200° C. for 20 min. The mixture was allowed to cool to room temperature (RT) over 10 min., then extruded using a hydraulic press (Carver, Inc.) at a pressure according to Table 2. The extrudate was calcined in air at 320° C. for 30 min.

TABLE 3

Tungsten-Modified SPA Catalysts

| Catalyst | Promoter | Promoter Reagent | Reagent Amount (g) | Extrusion Pressure (kPsi) | Promoter Amount (wt. %)[1] |
|---|---|---|---|---|---|
| SPA-18 | Tungsten | Tungstosilicic acid | 0.6 | 18-20 kPsi | 1.2 |
| SPA-19 | Tungsten | Phosphotungstic acid | 0.9 | 12-15 kPsi | 1.7 |

[1]Calculated as percentage of combined promoter and siliceous support material. Both materials had about 0.5% tungsten overall (calculated as oxide).

Example 5

SPA-Catalyzed 1-Butene Oligomerization

An SPA catalyst composition prepared according to Examples 1-4 or a commercially available SPA catalyst (Süd-Chemie C84-5) were placed in a reactor. A feed containing 30 wt. % 1-butene and 70 wt. % propane, maintained at a moisture level of 510 ppm, was passed through the catalyst bed at a linear hourly space velocity (LHSV) of 1.3 h$^{-1}$. The temperature and the pressure of the catalyst bed were maintained at 160° C. and 38 bars. Tables 4-7 show the 1-butene conversion after various times on stream. FIGS. 1-4 graphically show the data of Tables 4-7.

TABLE 4

1-Butene Conversion of SPA Catalyst Compositions

| Time on Stream (h) | 1-Butene Conversion (%) | | | | | |
|---|---|---|---|---|---|---|
| | C84-5 | SPA-C | SPA-1 | SPA-2 | SPA-3 | SPA-4 |
| 20 | 67.6 | 69.1 | 79.4 | 89.9 | 86.6 | 89.2 |
| 40 | 66.7 | 80.1 | 82.0 | 86.4 | 86.6 | 90.2 |
| 60 | 68.2 | 79.4 | 82.4 | 84.8 | 86.0 | 89.5 |
| 80 | 68.7 | 79.3 | 81.2 | 83.7 | 85.6 | 89.0 |
| 100 | 68.9 | 78.8 | 80.1 | 81.4 | 84.2 | 88.1 |
| 130 | 69.0 | 78.4 | 78.9 | 79.4 | 82.3 | 86.6 |

TABLE 5

1-Butene conversion with various silica-modified SPA catalysts

| Time (h) | 1-Butene Conversion (%) | | | | | | | | | |
|---|---|---|---|---|---|---|---|---|---|---|
| | C84-5 | SPA-C | SPA-7 | SPA-8 | SPA-9 | SPA-10 | SPA-11 | SPA-12 | SPA-13 | SPA-14 |
| 20 | 67.6 | 69.1 | 85.9 | 91.4 | 80.2 | 84.9 | 72.1 | 72.5 | 78.0 | 81.0 |
| 40 | 66.7 | 80.1 | 86.6 | 92.4 | 83.4 | 86.4 | 77.6 | 77.2 | 80.7 | 85.1 |
| 60 | 68.2 | 79.4 | 86.4 | 92.4 | 83.1 | 86.4 | 77.5 | 77.4 | 80.2 | 84.7 |
| 80 | 68.7 | 79.3 | 87.0 | 92.6 | 82.8 | 85.8 | 77.2 | 77.7 | 79.6 | 82.8 |
| 100 | 68.9 | 78.8 | 87.1 | 92.8 | 82.3 | 86.2 | 76.8 | 76.4 | 78.1 | 81.9 |
| 130 | 69.0 | 78.4 | 87.8 | 92.9 | 83.5 | 86.8 | 75.3 | 72.9 | 77.8 | 81.1 |

TABLE 6

1-Butene conversion with various clay-modified SPA catalysts

| Time | 1-Butene Conversion (%) | | | |
|---|---|---|---|---|
| (h) | C84-5 | SPA-C | SPA-16 | SPA-17 |
| 20 | 67.6 | 69.1 | 91.5 | 82.9 |
| 40 | 66.7 | 80.1 | 85.9 | 84.5 |
| 60 | 68.2 | 79.4 | 86.2 | 84.6 |
| 80 | 68.7 | 79.3 | 85.6 | 83.1 |
| 100 | 68.9 | 78.8 | 84.4 | 81.3 |
| 130 | 69.0 | 78.4 | 82.3 | 79.4 |

TABLE 7

1-Butene conversion with various tungsten-modified SPA catalysts

| | 1-Butene Conversion (%) | | |
|---|---|---|---|
| Time (h) | C84 5 | SPA-18 | SPA-19 |
| 15 | 61.5 | 85.8 | 88.6 |
| 42 | 66.8 | 82.7 | 83.8 |
| 69 | 70.7 | 83.3 | 91.3 |
| 97 | 71.0 | 82.1 | 87.0 |
| 125 | 71.9 | 80.9 | 86.1 |
| 152 | 73.1 | 80.5 | 86.2 |

Modified SPA catalysts yielded a stable 1-butene conversion higher than that of unmodified SPA catalysts. For several modified SPA catalysts, a stable 1-butene conversion between 85-90% was observed, which is an improvement over unmodified SPA catalysts of at least 10%.

Example 7

SPA-Catalyzed Propylene Oligomerization

Figure 5:
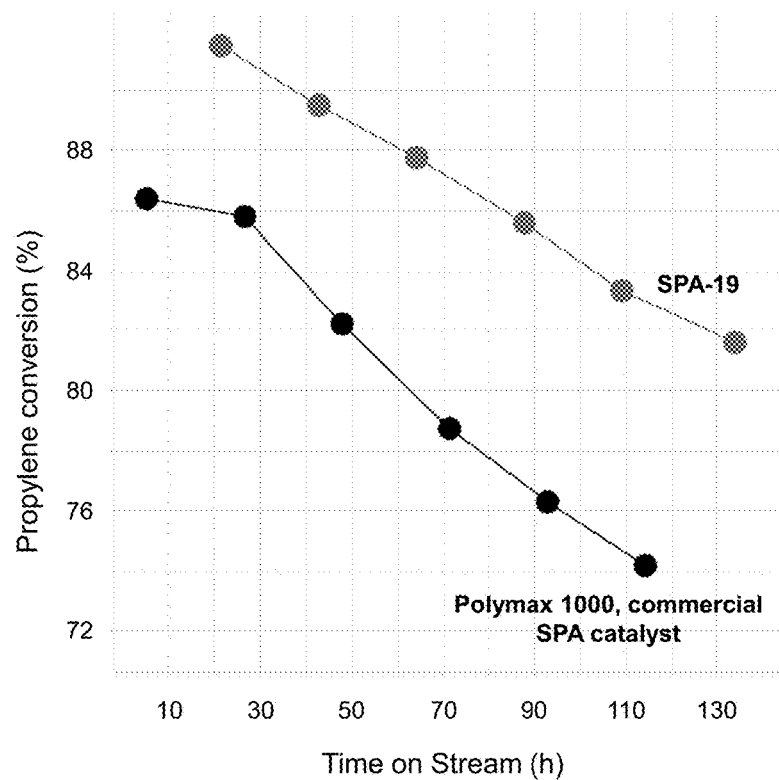
FIG. 5 is a graph of propylene conversion after various times on stream for propylene oligomerization for support-modified SPA catalyst (SPA-19) and a commercially available SPA catalyst (Polymax 1000), as described in Example 7.

SPA catalyst composition SPA-19 or a commercially available SPA catalyst (Polymax 1000) were placed in a reactor. A feed containing 55 wt. % propylene and 45 wt. % propane, maintained at a moisture level of 510 ppm, was passed through the catalyst bed at a linear hourly space velocity (LHSV) of 18 h$^{-1}$. The temperature and the pressure of the catalyst bed were maintained at 216° C. and 51.7 bars. Table 8 shows the propylene conversion after various times on stream; FIG. 5 presents this data graphically.

TABLE 8

Propylene conversion with tungsten-modified SPA catalyst

| | 1-Butene Conversion (%) | |
|---|---|---|
| Time (h) | Polymax 1000 | SPA-18 |
| 12 | 86.4% | 91.5% |
| 34 | 85.8% | 89.5% |
| 56 | 82.2% | 87.8% |
| 78 | 78.5% | 85.6% |
| 100 | 76.3% | 83.3% |
| 122 | 74.2% | 81.6% |

Here, too, the tungsten-modified SPA catalysts yielded a stable propylene conversion higher than that of unmodified SPA catalysts.

What is claimed is:

1. A calcined solid phosphoric acid catalyst composition comprising:
   one or more phosphoric acids;
   one or more silicon phosphates;
   optionally, one or more additional inorganic phosphates; and
   optionally, a siliceous support material,
   wherein the amount of phosphate in the calcined solid phosphoric acid catalyst composition is within the range of about 30 wt. % to about 85 wt. %, calculated as $P_2O_5$ on a calcined basis; and
   the amount of silicon in the calcined solid phosphoric acid catalyst composition is within the range of about 15 wt. % to about 70 wt. %, calculated as $SiO_2$ on a calcined basis; and
   wherein
   (i) the calcined solid phosphoric acid catalyst composition includes one or more promoters each selected from the group consisting of boron, bismuth, tungsten, silver, and lanthanum, present in an amount within the range of about 0.015 wt. % to about 5 wt. %, calculated as oxide on a calcined basis;
   (ii) the calcined solid phosphoric acid catalyst composition is the calcined product of a mixture comprising one or more of a silica-alumina clay, a silica fiber material and a silica-alumina fiber material, present in the mixture in an amount within the range of about 0.1 wt. % to about 15 wt. % on a calcined basis; or
   (iii) the calcined solid phosphoric acid catalyst composition is the calcined product of a mixture comprising fumed silica, present in the mixture in an amount within the range of about 0.1 wt. % to about 15 wt. % on a calcined basis.

2. The catalyst composition of claim 1, wherein at least one of the one or more promoters selected from the group consisting of boron, bismuth, tungsten, silver and lanthanum is present.

3. The catalyst composition of claim 2, wherein the atomic molar ratio of phosphorus to the total amount of boron, bismuth, tungsten, silver and lanthanum is within the range of about 1:0.05 to about 1:0.0001; and the atomic molar ratio of silicon to the total amount of boron, bismuth, tungsten, silver and lanthanum is within the range of about 1:0.05 to about 1:0.0001.

4. The catalyst composition of claim 2, wherein the atomic molar ratio of phosphorus to the total amount of boron, bismuth, tungsten, silver and lanthanum is within the range of about 1:0.005 to about 1:0.0005; and the atomic molar ratio of silicon to the total amount of boron, bismuth, tungsten, silver and lanthanum is within the range of about 1:0.005 to about 1:0.0005.

5. The catalyst composition of claim 1, wherein the calcined solid phosphoric acid catalyst composition is the calcined product of a mixture comprising the silica-alumina clay, the silica fiber material, and/or the silica-alumina fiber material.

6. The catalyst composition of claim 5, wherein the mixture includes a siliceous support material source, and wherein the total amount of the silica-alumina clay, silica fiber material, and the silica-alumina fiber material is within the range of about 0.1 wt. % to about 30 wt. % of the total amount of siliceous support material source and the silica-alumina clay, silica fiber material, and silica-alumina fiber material in the mixture.

7. The catalyst composition of claim 1, wherein the calcined solid phosphoric acid catalyst composition is the calcined product of a mixture comprising the fumed silica.

8. The catalyst composition of claim 7, wherein the mixture includes a siliceous support material source, and wherein the fumed silica is present in an amount within the range of about 0.5 wt. % to about 20 wt. % of the total amount of siliceous support material source and fumed silica in the mixture.

9. The catalyst composition of claim 1, wherein the total amount of the one or more phosphoric acids, the one or more silicon phosphates, the one or more promoters, silica-alumina clay, silica-alumina fiber, silica fiber, and fumed silica, and the optional siliceous support material is at least about 80 wt. %.

10. The catalyst composition of claim 1, wherein there are substantially no promoters other than boron, bismuth, tungsten, silver and lanthanum present.

11. The catalyst composition of claim 1, wherein substantially no promoters are present.

12. The catalyst composition of claim 1, wherein substantially no silica-alumina clay, silica fiber material or silica-alumina fiber material are present in the mixture calcined to make the composition.

13. The catalyst composition of claim 1, wherein substantially no fumed silica is present in the mixture calcined to make the composition.

14. The catalyst composition of claim 1, wherein the siliceous support material is at least 90 wt. % $SiO_2$.

15. The catalyst composition of claim 1, wherein the atomic molar ratio of phosphorus to silicon is within the range of about 1:1 to about 5:1; and
wherein the solid catalyst material comprises an amount of silicon orthophosphate and, optionally, an amount of silicon pyrophosphate, wherein the integrated XRD reflectance intensity ratio of silicon orthophosphate to silicon pyrophosphate in the solid catalyst material is at least about 5:1.

16. A method for preparing a solid phosphoric acid catalyst composition according to claim 1, the method comprising
providing a mixture comprising
a phosphate source present in an amount within the range of about 50 wt. % to about 85 wt. % on a calcined weight basis;
a siliceous support material source present in an amount within the range of about 15 wt. % to about 50 wt. % on a calcined weight basis; and
at least one of
(i) one or more sources of one or more promoters each selected from the group consisting of boron, bismuth, tungsten, silver, and lanthanum, present in an amount within the range of about 0.015 wt. % to about 5 wt. % on a calcined weight basis;
(ii) a silica-alumina clay, a silica fiber material, and/or an alumina-silica fiber material, present in an amount within the range of about 0.1 wt. % to about 15 wt. % on a calcined weight basis; and
(iii) fumed silica present in an amount within the range of about 0.1 wt. % to about 15 wt. % on a calcined weight basis;
forming the mixture; and
calcining the formed mixture.

17. The method of claim 16, wherein the formed mixture is calcined at a temperature within the range of about 200° C. to about 500° C.

18. The method of claim 16, wherein the total amount of phosphate source, the one or more promoters, silica-alumina clay, silica fiber material, silica-alumina fiber material, fumed silica, and the siliceous support material source is at least about 80 wt. % of the mixture on calcined weight basis.

19. The method of claim 16, wherein the phosphate source is a phosphoric acid; and
wherein the siliceous support material source is at least 90 wt. % $SiO_2$.

20. A catalyst composition made by the method of claim 16.

21. A method for olefin oligomerization or aromatic hydrocarbon alkylation, the method comprising contacting a hydrocarbon feed with the catalyst composition of claim 1.

22. The catalyst composition of claim 1, wherein the atomic molar ratio of phosphorus to silicon is within the range of about 2:1 to about 4:1.

\* \* \* \* \*